US 6,523,595 B1

(12) United States Patent
Milner et al.

(10) Patent No.: US 6,523,595 B1
(45) Date of Patent: Feb. 25, 2003

(54) METHOD OF AND APPARATUS FOR SEPARATING DISCRETE ELEMENTS FROM PRE-PERFORATED WEB FOR PLACEMENT ON PRODUCT WEB MOVING AT DIFFERENT SPEED

(75) Inventors: James Dell Milner, Appleton, WI (US); Robert Herrick Collins, Aiken, SC (US); James Grant Lee, Aiken, SC (US); David Allen Palzewicz, Kennesaw, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/389,544

(22) Filed: Sep. 3, 1999

(51) Int. Cl.⁷ .............................................. B32B 31/00
(52) U.S. Cl. ........................ 156/519; 156/160; 156/252; 156/265; 156/302; 225/2; 225/4; 225/5; 225/96; 225/100
(58) Field of Search ................................ 156/164, 163, 156/160, DIG. 33, 265, 302, 252, 519, 521, 559; 83/346; 225/4, 5, 2, 96, 100

(56) References Cited

U.S. PATENT DOCUMENTS

| 2,209,765 A | * | 7/1940 | Cormack ..................... 156/212 |
| 4,061,527 A | | 12/1977 | Traise ........................ 156/519 |
| 4,079,875 A | * | 3/1978 | Zodrow ........................ 225/96 |
| 4,726,876 A | | 2/1988 | Tomsovic, Jr. .............. 156/552 |
| 5,716,478 A | | 2/1998 | Boothe et al. .............. 156/302 |
| 5,759,340 A | * | 6/1998 | Booth et. ..................... 156/519 |
| 5,791,219 A | * | 8/1998 | Ochsner ........................ 83/331 |

FOREIGN PATENT DOCUMENTS

CH            268 984         10/1950

* cited by examiner

Primary Examiner—Linda Gray
(74) Attorney, Agent, or Firm—Wilhelm Law Service; Thomas D. Wilhelm

(57) ABSTRACT

A method and apparatus are provided for separating a discrete element from a first substrate web, moving at a first speed, and placing the discrete element on a second substrate web, moving at a second speed. The apparatus includes a first station, wherein perforations are made in the first substrate web, and a second station, wherein the discrete element is separated from the first substrate web at a line of perforations and the discrete element is transferred to a positioned on the second substrate web. The first station includes a perforation cutter assembly and conveyer assembly. The perforation cutter assembly includes first and second rollers with a cutting blade, with a discontinuous edge, and an anvil surface, respectively, to make perforations in the first substrate web. The second station includes a separation and transfer mechanism having separation and transfer segments for separating and transferring the discrete element from the first substrate web to the second substrate web. The method includes the steps of: making perforations across a width, at least partially through a thickness, and at predetermined spaced apart intervals along a length of the first substrate web; separating the discrete element from the first substrate web along a first line of the perforations; and placing the discrete element on the second substrate web.

10 Claims, 3 Drawing Sheets

METHOD OF AND APPARATUS FOR SEPARATING DISCRETE ELEMENTS FROM PRE-PERFORATED WEB FOR PLACEMENT ON PRODUCT WEB MOVING AT DIFFERENT SPEED

FIELD OF THE INVENTION

The present invention generally relates to a method of and apparatus for manipulating two webs moving at different speeds and more particularly, to a method of and apparatus for separating discrete elements from a first substrate web moving at a first speed, after the first substrate web has been pre-perforated, and placing the discrete element separated from the first substrate web onto a second substrate web moving at a second speed.

BACKGROUND OF THE INVENTION

Conventionally, absorbent articles for personal care usages, such as infant diapers, child training pants, adult incontinence garments, feminine sanitary napkins, and similar products for storing fluid bodily exudates, have been manufactured on an assembly line. The assembly line manufacture of these absorbent articles has involved manipulating first and second substrate webs moving at first and second different speeds, respectively. A number of machines and processes are known in the prior art for cutting discrete components from a first substrate web, traveling at a slower speed, and transferring the cut discrete components to a second substrate web, traveling at a faster speed. Many of these known machines and processes provide for the cutting of the discrete components at a point separated from the mechanism for transferring the cut component to the second web. In this situation, it often becomes difficult to maintain proper positioning and orientation of the cut component between the cutting operation and the placement of the cut component on the second substrate web. This problem is exacerbated in those cases where placement and orientation of the cut component on the second web are critical.

A solution to this problem has been proposed in the prior art which involves the cutting of the discrete components from the first substrate web after the first substrate web has been placed on a transfer roller. Indeed, the use of a cutting and transfer mechanism, such as an oscillating cam adjusted roller or OSCAR module, is taught in U.S. Pat. No. 5,716,478 (hereinafter "the '478 patent"), issued to Boothe et al. on Feb. 10, 1998, and entitled Apparatus And Method For Applying Discrete Parts Onto A Moving Web. The '478 patent discloses how discrete elements or component parts of an absorbent article being manufactured, such as absorbent cores or inserts, leg elastics, waist elastics, tapes, and other fasteners including hook and loop materials or snaps, on a first continuously moving substrate web, may be cut from the first substrate web and applied to a second continuously moving substrate web of interconnected articles which is moving at a different speed on an assembly line.

The '478 patent also discloses that the cutting of the discrete elements or component parts from the first substrate web is most preferably accomplished by use of a knife roll. The knife roll includes a plurality of cutting edges rotating about a shaft. The cutting edges of the knife roll cut the first substrate web into discrete elements or component parts at the junction between adjacent transfer segments of a transfer mechanism or OSCAR module.

However, the apparatus and method of the '478 patent have certain drawbacks or problems associated therewith, because the cutting of the first substrate web into discrete elements or component parts involves competing concerns. On one hand, it is advantageous that the discrete elements or component parts are not cut from the web too early in the process in order to maintain the integrity of the web and thus, allow for easier transportation of the web from place to place. On the other hand, not cutting the discrete elements from the first substrate web early enough creates complications with adhesive application, if necessary, and also the location of the cutting equipment becomes difficult due to the confined space within which it must be positioned.

The '478 patent teaches that the cutting of the first substrate web into discrete elements occurs at the junction between two adjacent transfer segments of the OSCAR module. This creates problems because cutting is typically done against a surface, such as an anvil, but as there is no anvil to cut against on the OSCAR module, if the rotation of the knife roll gets out of phase with the separation of the transfer segments, the knife roll may nick or damage the outer arched surface of the transfer segment. Thus, the useful life of the transfer segments may be shortened causing great expense for labor and parts in replacement and also down time of the assembly line.

It would be desirable if a method of and apparatus for separating a discrete element from a first substrate web moving at a first speed on an assembly line could be provided, without the need for a cutting device at a cutting station to cut the discrete element from the first substrate web, prior to placement of the discrete element on a second substrate web moving at a second speed.

SUMMARY OF THE INVENTION

In response to the discussed difficulties and problems encountered with respect to the prior art devices and methods, the present invention provides a method of and an apparatus for separating a discrete element from a first substrate web and placing the discrete element on a second substrate web moving at a different speed than the first substrate web.

In one aspect of the present invention, an apparatus for separating a discrete element from a first substrate web moving at a first speed and applying the discrete element onto a second substrate web moving at a second speed is provided. The apparatus includes a first station for making perforations across a width, at least partially through a thickness, and at predetermined spaced apart intervals along the first substrate web. The apparatus also includes a second station for separating the discrete element from the first substrate web at a first line of the perforations and then, placing the discrete element on the second substrate web.

In another aspect of the present invention, a method of separating a discrete element from a first substrate web moving at a first speed and applying the discrete element onto a second substrate web moving at a second speed is provided. The method includes the steps of: making perforations across a width, at least partially through a thickness, and at predetermined spaced apart intervals along a length of the first substrate web; separating the discrete element from the first substrate web along a first line of the perforations; and placing the discrete element on the second substrate web.

BRIEF DESCRIPTION OF THE DRAWING FIGURES

The present invention will be more fully understood and further advantages will become apparent when reference is made to the following detailed description of the invention and the accompanying drawings wherein like numerals represent like elements. The drawings are merely representative and are not intended to limit the scope of the appended claims.

FIG. 1 is a representative view of a first embodiment of the apparatus aspect of the present invention.

DETAILED DESCRIPTION OF THE INVENTION

The present invention provides a method of and apparatus for separating a discrete element from a first, pre-perforated substrate web moving at a first speed and placing the discrete element that has been separated from the first substrate web onto a second substrate web moving at a second speed. The method and apparatus are particularly useful in the manufacture of absorbent articles, such as infant diapers, child training pants, adult incontinence garments, feminine sanitary napkins, or similar products for storing fluid bodily exudates, wherein a discrete element or component part, such as an absorbent core or insert member and a waist elastic member, needs to be separated from a first, pre-perforated web moving at a first speed and then, the discrete element or component part of the absorbent article needs to be applied to a second, product web of interconnected absorbent articles. However, it is readily apparent that the method and apparatus would be suitable for applying any part, separated from one web, to a substrate web.

Figure 1:
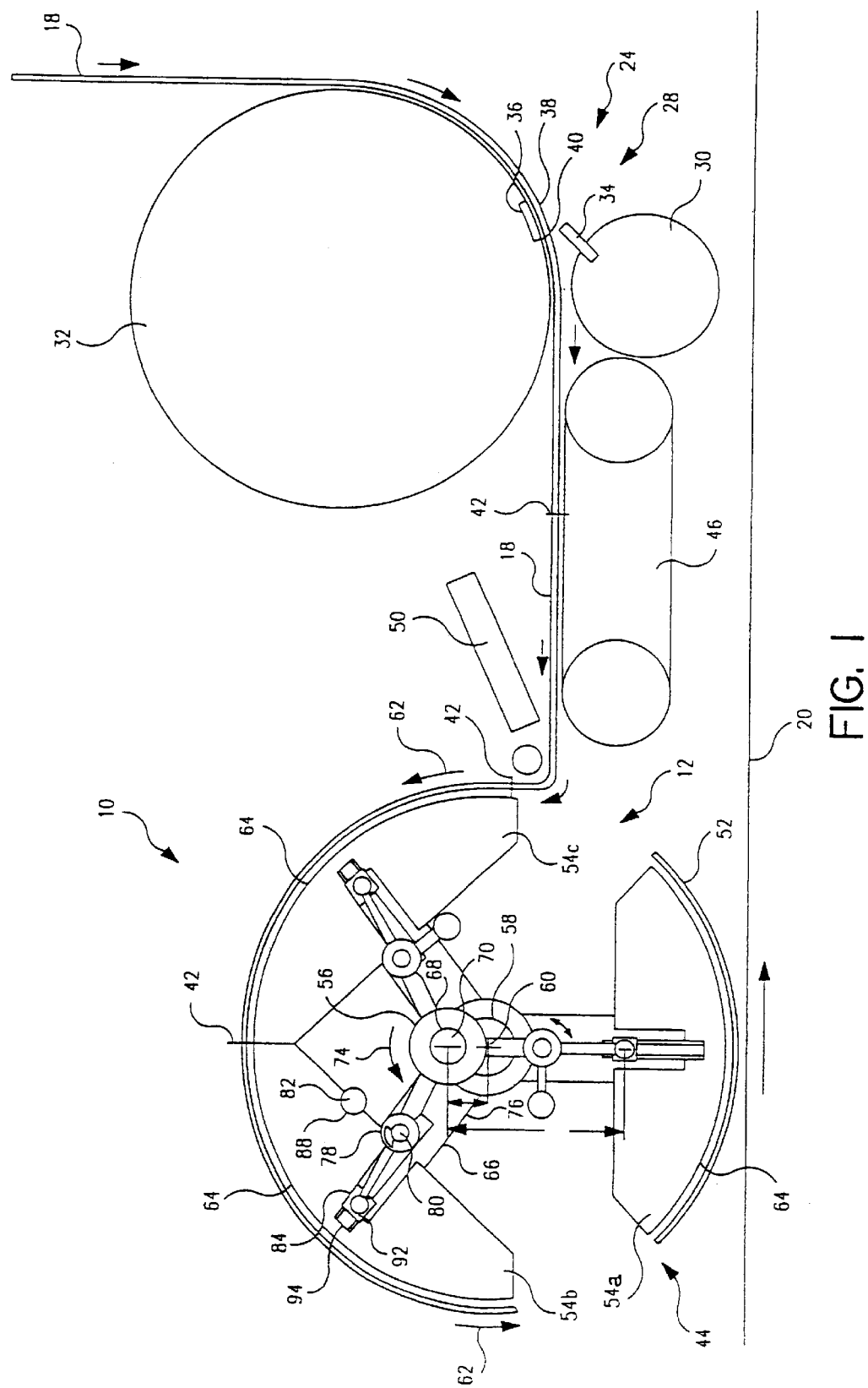
Figure 2:
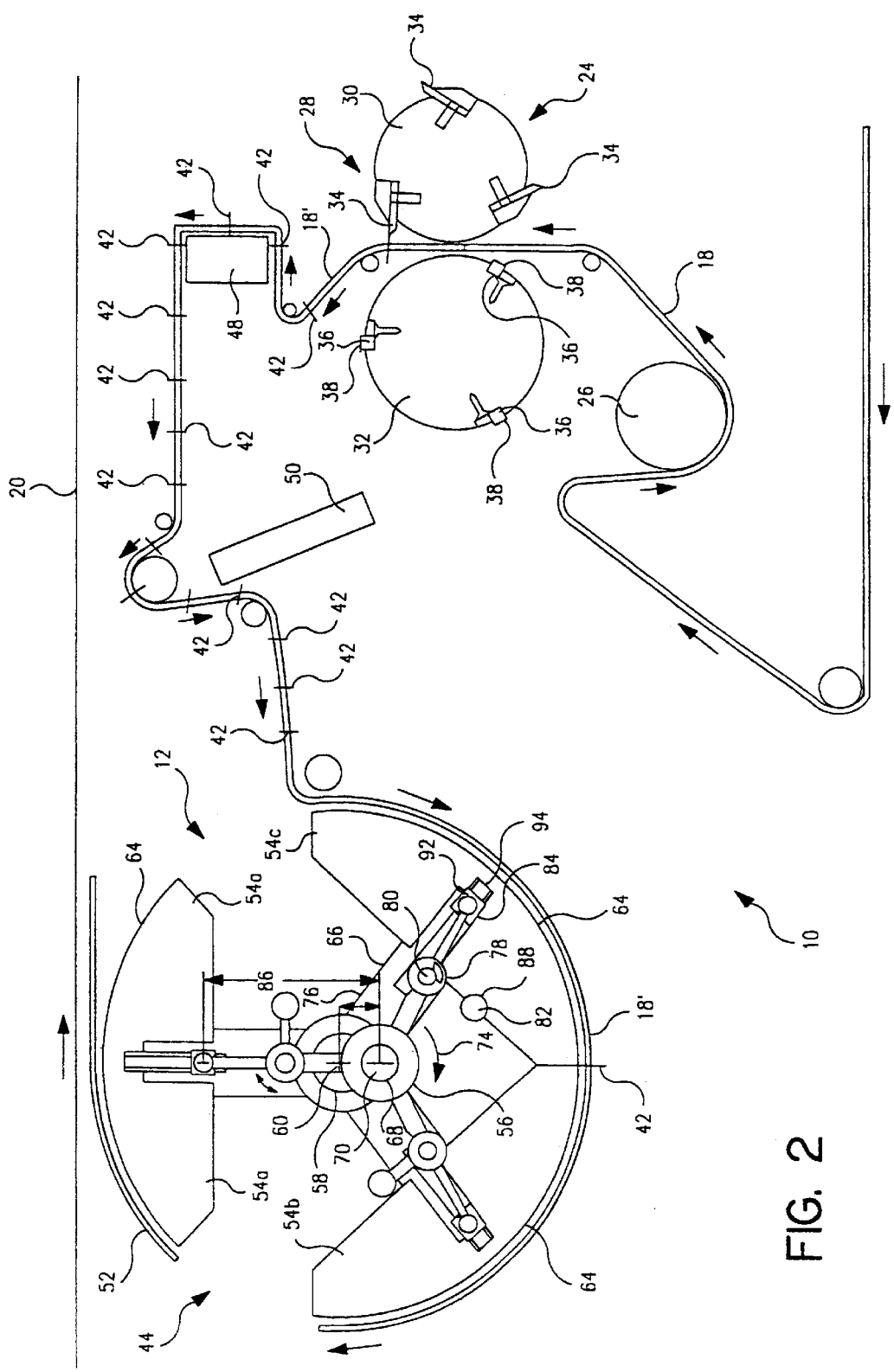
FIG. 2 is a representative view of a second embodiment of the apparatus aspect of the present invention.

Referring to FIGS. 1 and 2, first and second embodiments, respectively, of the apparatus 10 of the present invention are shown schematically. It should be noted that both the first and second embodiments of the apparatus 10 of the present invention employ a separation and transfer mechanism 12. The separation and transfer mechanism 12 is most preferably an oscillating cam adjusted roller or OSCAR module as is taught in the '478 patent discussed above and as will be described in more detail below.

The first embodiment of the apparatus 10 of the present invention, as illustrated schematically in FIG. 1, is particularly well suited for the manufacture of an absorbent article 14 (which will be described in more detail below in reference to FIG. 5), such as an adult incontinence garment, wherein a plurality of a certain component of the incontinence garment, such as the absorbent core or insert member 16, are transported on a first substrate web 18, which is moving at a first speed on an assembly line, and must somehow be separated from the first substrate web 18 and then, transferred and positioned on a second substrate web 20, such as a plurality of interconnected incontinence garment products or panties, which is moving at a second speed through the assembly line.

The second embodiment of the apparatus 10 of the present invention, as illustrated schematically in FIG. 2, is particularly well suited for the manufacture of an absorbent article 14, such as an infant diaper, wherein a plurality of a certain component of the diaper, such as a pre-stretched waist elastic members 22, are transported in a pre-stretched orientation on a first substrate web 18, which is moving at a first speed on an assembly line, and must somehow be separated from the first substrate web 18 and then, while remaining in the stretched orientation, be transferred and positioned onto a second substrate web 20, such as a plurality of interconnected adult incontinence garment products or panties, which is moving at a second speed through the assembly line.

In FIG. 1, the first embodiment of the apparatus 10 of the present invention shows the unperforated first substrate web 18 as preferably initially fed from above to the apparatus 10, from a supply roll (not shown), although other initial orientations of the supply roll (not shown) are possible. The unperforated first substrate web 18 is transported downwardly on a conveyor assembly (not shown) to a first station 24.

In FIG. 2, the second embodiment of the apparatus 10 of the present invention shows the unperforated first substrate web 18 as preferably initially located somewhere below the apparatus 10, although other initial orientations are possible. The unperforated first substrate web 18 is transported upwardly by means of a web feed drive roller 26 to the first station 24.

In both the first and second embodiments shown in FIGS. 1 and 2, the first station 24 includes a perforation cutter assembly 28. The term "perforation" is defined as a series of small incisions, slits, openings, or holes of any shape (whether round, rectangular, or other) alternating with spaces of uncut material to define a line along which separation is facilitated. Although the incisions, slits, openings, or holes of the perforations may be entirely through the thickness of the material in which they are placed, they may also be only partially through the thickness as long the deepness of the incision, slit, opening, or hole into the thickness of the material is enough to facilitate easier separation.

The perforation cutter assembly 28 of both the first and second embodiments include first and second rollers 30, 32. In the first embodiment shown in FIG. 1, the first roller 30 is shown as being of a much smaller diameter than the diameter of the second roller 32, although the first and second rollers 30, 32 may be of equal or nearer equal diameters. In the second embodiment shown in FIG. 2, the first roller 30 has only a slightly smaller diameter than the diameter of the second roller 32, although the diameters of the first and second rollers 30, 32 may be more disproportionate, depending upon the desired distance between perforations along the length of the first substrate web 18.

In both the first and second embodiments of the apparatus 10 of the present invention shown in FIGS. 1 and 2, the first roller 30 has at least one discontinuous cutting blade 34 mounted at an angle thereon and extending outwardly from the circumference thereof. The term "discontinuous" is defined as not continuous, or in the context of an edge, an edge that alternatingly continues for some distance and then lapses for some distance such as a crenellated, sinusoidal or corrugated edge, wherein the alternating ridges and grooves may be squarish, triangular, etc. rather than curved. The second roller 32 has a plurality of anvil members 36, of the type having relatively flat surfaces 38 for being cut against by a blade or knife, mounted so as to be partially embedded in the outer circumference thereof with the flat surface 38 extending slightly outwardly.

Figure 3:
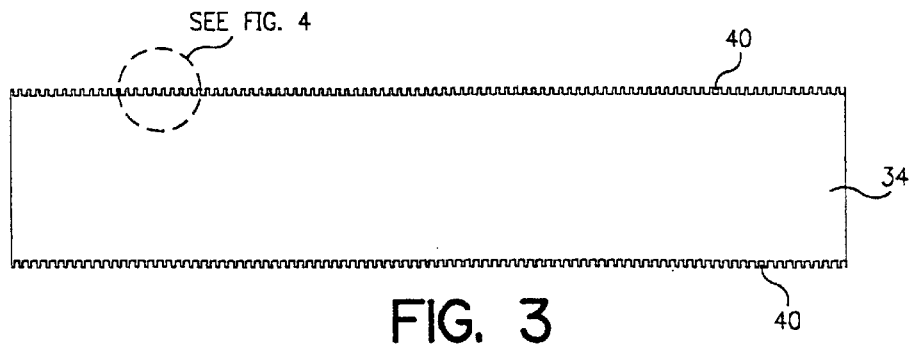
FIG. 3 is a front view of a discontinuous cutting blade with a discontinuous cutting edge for making perforations.
Figure 4:
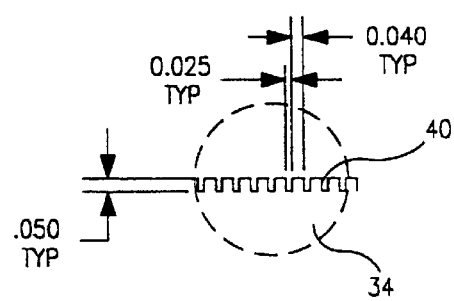
FIG. 4 is an enlarged view of circle 4—4 of FIG. 3 showing details of the discontinuous surface of the discontinuous cutting blade.

Referring to FIGS. 3 and 4, the discontinuous cutting blade 34 used to make perforations in the first web 18 is illustrated. The discontinuous cutting blade 34 is preferably formed from a flat piece of metal plate and is most preferably rectangular in shape so as to have two short sides and two long sides. The two long sides have discontinuous cutting edges 40 along the outer periphery thereof. The discontinuous cutting edges 40 are somewhat "toothed" in appearance. Indeed, in the preferred embodiment each "tooth" is approximately 0.050" high and 0.040" wide and spaced apart at 0.025" wide intervals, although these dimensions may change depending upon the type of material to be perforated and other variables. It should be noted that the discontinuous cutting edges 40 of the discontinuous cutting blade 34 are designed to leave a clean edge upon separation and to maintain a balance between integrity of the pre-perforated web 18' up to the point of separation and substrate appearance after separation from the web 18'. For example, a web requiring approximately 7 pounds per linear inch breaking tensile strength would require a discontinuous cutting blade 34 with discontinuous cutting edges 40 spaced about 0.025" to 0.040" apart to achieve a resultant separation tear strength of 2 pounds per linear inch. Most advantageously, the discontinuous cutting blade 34 is preferably symmetrical across its lateral and longitudinal central axis so that the orientation of the discontinuous cutting blade 34 may be changed for cutting along a different part of the discontinuous cutting edge 40 when the discontinuous cutting blade 34 becomes dull to save money in replacement costs.

The second roller 32 of the first and second embodiments of the apparatus 10 of the present invention has at least one anvil member 36 of the type having a flat surface 38 for being cut against by a blade or knife. The first and second rollers 30, 32 are timed to rotate with respect to each other so that the discontinuous cutting edge 40 of the discontinuous cutting blade 34 of the first roller 30 contacts the flat surface 38 of the anvil member 36 of the second roller 28 in order to make lines of perforations 42 across the width of the first substrate web 18.

After the first substrate web 18 has passed through the perforation cutter assembly 28 of the first and second embodiments of the apparatus 10 of the present invention, a pre-perforated first substrate web 18' is formed which must be transported from the first station 24 to a second station 44. As is shown in FIG. 1, the first embodiment of the apparatus 10 of the present invention uses an elongate conveyor assembly 46 to transport the pre-perforated first substrate web 18' from the first station 20 to the second station 44.

With respect to the second embodiment of the apparatus 10 of the present invention as is shown in FIG. 2, a web guide 48 may be located between the first and second stations 24, 44. The web guide 48 is used to help keep the pre-perforated first substrate web 18' centered during its conveyance through the assembly line. Alternatively, if a web guide 48 is provided, it may be located at some point prior to the first station 24.

With respect to both the first and second embodiment of the apparatus 10 of the present invention as is shown in FIGS. 1 and 2, an adhesive applicator assembly 50 may be located between the first and second stations 24, 44. The adhesion applicator assembly 50 is used to apply adhesive to a first outer surface of the pre-perforated first substrate web 18', which first outer surface is the surface of the pre-perforated first substrate web 18' which does not come into contact with the outer periphery of the separation and transfer mechanism 12 located at the second station 44.

Both the first and second embodiments of the apparatus 10 of the present invention as shown in FIGS. 1 and 2, respectively, include a second station 44 where discrete elements or component parts 52 are separated from the pre-perforated first substrate web 18' and then, transferred and positioned onto the second substrate web 20 by the separation and transfer mechanism 12.

The separation and transfer mechanism 12 is most preferably an oscillating cam adjusted roller or OSCAR module as taught in U.S. Pat. No. 5,716,478 issued to Boothe et al. on Feb. 10, 1998. The separation and transfer mechanism 12 may include a plurality of separation and transfer segments 54. More particularly, the illustrated example of the separation and transfer mechanism 12 in FIGS. 1 and 2 have first, second, and third separation and transfer segments 54a, 54b, and 54c. However, it should be readily understood that the apparatus 10 may include any number of separation and transfer segments 54 depending upon the different web speeds and desired placement and size of the discrete element 52. For instance, a working model of the apparatus 10 of the first embodiment built by applicant had a separation and transfer mechanism 12 with five separation and transfer segments.

The first, second, and third separation and transfer segments 54a, 54b, and 54c are configured to receive the pre-perforated first substrate web 18' from the conveyor assembly 46 at the first station 24, separate a discrete element 52 from the pre-perforated first substrate web at a line of perforations, and apply the discrete element 52 to the second substrate web 20. Each of first, second, and third separation and transfer segments 54a, 54b, and 54c is rotated by a drive ring 56 such that the surface speed of each of first, second, and third separation and transfer segments 54a, 54b, and 54c is substantially equal to the speed of the first substrate web 18 as the discrete elements 52 are received and substantially equal to the speed of the second substrate web 20 as the discrete elements 52 are applied.

Each of first, second, and third separation and transfer segments 54a, 54b, and 54c is coaxially supported and rotatably connected to a common idler shaft 58 on a first axis 60. First, second, and third separation and transfer segments 54a, 54b, and 54c are rotated about the first axis 60 in the direction indicated by the arrow 62 associated therewith. Each of first, second, and third separation and transfer segments 54a, 54b, and 54c include an outer surface 64 and a support member 66 which is rotatably connected to the idler shaft 58 such that each of first, second, and third separation and transfer segments 54a, 54b, and 54c can be rotated independently. The radial inner end of the support member 66 of each of first, second, and third separation and transfer segments 54a, 54b, and 54c may be rotatably connected to the idler shaft 58 by any technique known to those skilled in the art such as, for example, using conventional bearings. Similarly, the other components of the apparatus 10 of the present invention can be rotatably connected together employing such conventional techniques.

The outer surface 64 of each of first, second, and third separation and transfer segments 54a, 54b, and 54c travels along and defines a common circumferential path that allows the discrete elements 52 to be received and applied to the second substrate web 20. The outer surface 64 is configured to receive at least one discrete element 52 and apply the discrete element 52 to the second substrate web 20 each revolution. For example, if the apparatus 10 of the present invention is being used to apply pre-stretched waist elastic members 22 to a continuously moving product web of interconnected disposable diapers as in the second embodiment to be explained in more detail below, the outer surface 64 of each of first, second, and third separation and transfer segments 54a, 54b, and 54c may be configured to receive the two segments of pre-stretched waist elastic members 22 and apply the waist elastic members 22 along the waist opening regions on each diaper. The outer surface 64 of each of first, second, and third separation and transfer segments 54a, 54b, and 54c may also be configured to rotate the discrete elements 52 before the discrete elements 52 are applied to the second substrate web 20. For example, the outer surface 64 of each of first, second, and third separation and transfer segments 54a, 54b, and 54c may be connected to a turning mechanism (not shown) which is configured to rotate the discrete elements 52 before being applied. Such a configuration is particularly desirable for applying waist elastic members 22 to a continuously moving web of interconnected disposable diapers.

The outer surface 64 of each of first, second, and third separation and transfer segments 54a, 54b, and 54c may be textured to define a surface roughness which assists in gripping and maintaining the discrete elements 52 on the outer surface 64. Such a configuration is particularly desirable when the discrete elements 52 are elongated waist elastic members 22. As used herein, the term "surface roughness" is the surface roughness of a material as determined by conventional methods known to those skilled in the art. One such method utilizes a profilometer to detect the surface roughness. The stylus of the profilometer is drawn across the textured surface a distance of 1.27 centimeters (hereinafter "cm"). The profilometer measures the number of Peaks and valleys on the surface as well as the magnitude of each. The profilometer automatically calculates the surface roughness as a Roughness Average (RA) which is the arithmetic average of the measured profile height deviations taken within the sampling length and measured from the graphical centerline. Outer surface 64 of each of first, second, and third separation and transfer segments 54a, 54b, and 54c may define a surface roughness of at least about 3 micrometers (hereinafter "$\mu$m"). Desirably, at least about 10 $\mu$m and more desirably, at least about 15 $\mu$m. For example, the outer surface 64 may have a surface roughness of from about 5 $\mu$m to about 50 $\mu$m and desirably from about 10 $\mu$m to about 20 $\mu$m. To achieve the surface roughness, the outer surface 64 of each of first, second, and third separation and transfer segments 54a, 54b, and 54c may also include a coating such as a plasma coating as are known to those skilled in the art. When the discrete elements 52 being received and applied by first, second, and third separation and transfer segments 54a, 54b, and 54c are elongated elastic parts, it is desirable that the outer surface 64 have a plasma coating which defines a surface roughness of at least about 5 $\mu$m. To assist in maintaining the discrete elements 52 on the outer surface 64 of each of first, second, and third separation and transfer segments 54a, 54b, and 54c, the outer surface 64 may also include a plurality of holes therein through which a relatively low pressure or vacuum can be drawn. The use of such vacuum is particularly desirable when the apparatus 10 of the present invention is used to receive and apply discrete elements 52 which are elongated elastic parts such as waist elastics for application on disposable diapers. The number and pattern of the holes through which the vacuum may be drawn may vary depending upon the size of the first, second, and third separation and transfer segments 54a, 54b, and 54c, the shape and size of the discrete elements 52, and the desired location of the discrete elements 52 on the first, second, and third separation and transfer segments 54a, 54b, and 54c. If vacuum is desired, typically, only a relatively small amount of vacuum is needed to assist the rough outer surface 64 of the first, second, and third separation and transfer segments 54a, 54b, and 54c to maintain the discrete elements 52 on the outer surface 64. For example, typically no more than about 20" of water and desirably only from about 0" to about 10" of water are required to assist the rough outer surface 64. Applicants have discovered that, when compared to conventional methods which use relatively high levels of vacuum to grip the parts, the combination of the rough outer surface 64 and the relatively low level of vacuum of the apparatus 10 of the present invention provide improved control and placement of the discrete elements 52 on the second substrate web 20 at a relatively lower cost.

If vacuum is desired, the vacuum may be drawn through the holes in the outer surface 64 by one or more sources of vacuum using conventional techniques for drawing a vacuum as are known to those skilled in the art. The vacuum to each of first, second, and third separation and transfer segments 54a, 54b, and 54c may also be controlled such that a vacuum is only being drawn from the outer surface 64 of each of first, second, and third separation and transfer segments 54a, 54b, and 54c for the period of its rotation when the discrete elements 52 are located on the outer surface 64. For example, the vacuum may be activated just prior to the discrete elements 52 being received and inactivated immediately after the discrete elements 52 are applied to the second substrate web 20.

The dimensions of separation and transfer segments 54 will vary depending upon the desired number of separation and transfer segments to be used and the size and shape of the discrete elements 52 being transferred. For example, when the apparatus 10 includes first, second, and third separation and transfer segments 54a, 54b, and 54c as representatively illustrated in FIGS. 1 and 2, each of first, second, and third separation and transfer segments 54a, 54b, and 54c may have an outer peripheral arc length spanning from about 20° to about 120°, an outer radius of from about 5 cm to about 50 cm, and a width of from about 5 cm to about 40 cm.

Both the first and second embodiments of the apparatus 10 of the present invention, as representatively illustrated in FIGS. 1 and 2, respectively, further comprises a drive ring 56 which is configured to rotate each of first, second, and third separation and transfer segments 54a, 54b, and 54c at a variable speed. The inner radial end of the drive ring 56 is rotatably connected to a fixed shaft 68 on a second axis 70. The drive ring 56 is configured to be rotated at a constant speed about the second axis 70 by a driving means (not shown) in the direction indicated by the arrow 74 associated therewith. The driving means (not shown) may include a motor operatively connected through suitable gearing and drive belts to the drive ring 56. In use, the motor rotates the drive ring 56, which in turn rotates each of first, second, and third separation and transfer segments 54a, 54b, and 54c at the desired variable speed.

To provide the desired variable speed of each first, second, and third separation and transfer segments 54a, 54b, and 54c, the second axis 70 of the drive ring 56 is offset from the first axis 60 of each of first, second, and third separation and transfer segments 54a, 54b, and 54c by an offset distance 76. The offset distance 76 between the first axis 60 and the second axis 70 may be any distance which provides the desired variations in, the speed of the outer surface 64 of each of first, second, and third separation and transfer segments 54a, 54b, and 54c. For example, the offset distance 76 may be at least about 0.1 cm, desirably from about 0.1 cm to about 7.5 cm and more desirably from about 2.5 cm to about 5 cm.

The apparatus 10 further comprises at least one coupler arm 78 which is pivotally connected to the drive ring 56 about a pivot point 80. The apparatus 10 typically includes one coupler arm 78 for each of first, second, and third separation and transfer segments 54a, 54b, and 54c. Accordingly, in the apparatus 10 as representatively illustrated in FIGS. 1 and 2 which includes first, second, and third separation and transfer segments 54a, 54b, and 54c, three coupler arms 78 independently connect the drive ring 56 to each respective separation and transfer segment 54. The coupler arms 78 are pivotally connected to the drive ring 56 about pivot points 80 which are selectively located to provide the desired speeds for each of first, second, and third separation and transfer segments 54a, 54b, and 54c. The pivot points 80 for the coupler arms 78 are located the same distance radially outwardly from second axis 70 of drive ring 56. In such a configuration, the pivot points 80 rotate at a constant speed along a common circumferential path as the drive ring 56 is rotated at a constant speed. The coupler arms 78 may be pivotally connected to the drive ring 56 by conventional means known to those skilled in the art. For example, a bearing which is commercially available from SKF Industries, Inc., a business having offices located in King of Prussia. Pa., may be used to pivotally connect the coupler arms 78 to the drive ring 56 at the pivot points 80.

Each coupler arm 78, as representatively illustrated in FIGS. 1 and 2, includes a cam end 82 and a crank end 84 which extend radially outward from the pivot point 80. The cam end 82 and crank end 84 are designed to remain at a fixed angle relative to each other. For example, a first line extending through the pivot point 80 and the cam end 82 and a second line extending through the pivot point 80 and the crank end 84 may define an angle of from about 30° to about 180° and desirably from about 60° to about 120° to provide, the desired variable speed. The cam end 82 of each coupler arm 78 is configured to follow a predetermined curvilinear path and the crank end 84 of each coupler arm 78 is slidably connected to one of first, second, and third separation and transfer segments 54a, 54b, and 54c. As the drive ring 56 is rotated, the cam end 82 of each coupler arm 78 is guided along the curvilinear path and the crank end 84 of each coupler arm 78 slidably engages one of first, second, and third separation and transfer segments 54a, 54b, and 54c, thereby pivoting the coupler arm 78 about the pivot point 80. The pivoting of the coupler arm 78 and the offset crank motion of the drive ring 56 vary the effective drive radius 86 of each of first, second, and third separation and transfer segments 54a, 54b, and 54c and rotate each of first, second, and third separation and transfer segments 54a, 54b, and 54c at a variable speed. Preferably, each coupler arm 78 is configured to pivot at least about 5° and desirably from about 20° to about 60° as the drive ring 56 is rotated to provide the desired changes in the effective drive radius 86 and rotation of each first, second, and third separation and transfer segments 54a, 54b, and 54c.

The cam end 82 of each coupler arm 78 may be guided along the curvilinear path by any means known to those skilled in the art. The cam end 82 may include a cam follower 88 which is connected to the radially outward end of the cam end 82 and configured to follow the profile of a cam mechanism (not shown). In such a configuration, the profile of the cam mechanism (not shown) can be readily changed to change the desired speed output. Suitable cam followers 88 and cam mechanisms (not shown) are known to those skilled in the art. For example, the cam follower 88 may be one commercially available from INA, a business having offices located in Fort Mills. N.C., under the trade designation NUKR 35. A suitable cam mechanism (not shown) may be manufactured with any desired profile by methods known to those skilled in the art.

The crank end 84 of each coupler arm 78 may be slidably connected to each of first, second, and third separation and transfer segments 54a, 54b, and 54c by any means known to those skilled in the art. An inwardly grooved slide member 92 may be pivotally connected to the radially outward end of the crank end 84 of each coupler arm 78. Each slide member 92 is configured to slide along a rail member 76 which is connected to the support member 66 of each of first, second, and third separation and transfer segments 54a, 54b, and 54c. Each rail member 94 projects outwardly from one of first, second, and third separation and transfer segments 54a, 54b, and 54c and may be positioned on one of first, second, and third separation and transfer segments 54a, 54b, and 54c in any alignment which provides the desired speeds thereof. Suitable complementary slide members 92 and rail members 94 are known to those skilled in the art. For example, the slide member 92 and rail member 94 combination may be one commercially available from Star Linear Systems. Inc., a business having offices located in Charlotte, N.C., under the trade designation Ball Rail System-1651-15. Alternatively, the crank end 84 of each coupler arm 78 may include a groove therein which is configured to slidably engage a cam follower 88 located on one of first, second, and third separation and transfer segments 54a, 54b, and 54c.

The apparatus 10 may further include a turning mechanism (not shown) for rotating the discrete elements 52 before they are applied to the second substrate web 20. Any mechanism which provides the desired rotation of the discrete elements 52 can be used. For example, one suitable mechanism is a barrel cam as are well known to those skilled in the art. Thus, in use, the discrete elements 52 may be received by one of first, second, and third separation and transfer segments 54a, 54b, and 54c while oriented in one direction and subsequently, be rotated by the turning mechanism (not shown) before being applied to the second substrate web 20. The turning mechanism (not shown) can be configured to rotate the discrete elements 52 any amount before they are applied. For example, the turning mechanism (not shown) may be configured to rotate the discrete elements 52 from about 1° to about 180° and desirably from about 1° to about 90° before they are applied depending upon the desired orientation of the discrete elements 52 on the second substrate web 20. Such a turning mechanism (not shown) is particularly useful when applying waist elastics to a product web of interconnected disposable absorbent articles.

It will be apparent that the discrete elements 52 may be adhered to the second substrate web 20 by means of an adhesive applied in a selected pattern to the surface of the discrete elements 52, or by any other suitable means for adhering the discrete elements 52 to the second substrate web 52.

The use of the combination of the offset drive ring 56 and pivoting coupler arm 78 to drive the first, second, and third separation and transfer segments 54a, 54b, and 54c in the apparatus 10, as representatively illustrated in the various aspects of the invention described above, provides an inexpensive and adaptable method for separating discrete elements or component parts 52 from a pre-perforated first substrate web 18' traveling at a first speed and applying the discrete elements or component parts 52 to a second substrate web 18 traveling at a second, different speed. The design of the drive ring 56 and coupler arm 78 can be analytically determined to obtain the desired output function which can include variable angular velocities with fixed speed dwells. For example, the speed profile of an example of an apparatus 10 has first, second, and third separation and transfer segments 54a, 54b, and 54c which can be configured to rotate through a period of low speed dwell, acceleration, high speed dwell, and deceleration, in each revolution.

As the offset drive ring 56 rotates at a constant speed, each coupler arm 78 pivots about the pivot points 80 as the cam end 82 of the coupler arm 78 is guided along the profile of the cam mechanism (not shown) and the crank end 84 of the coupler arm 78 slidably engages one of first, second, and third separation and transfer segments 54a, 54b, and 54c. As a result, the effective drive radius 86 for each of first, second, and third separation and transfer segments 54a, 54b, and 54c is varied thereby varying the surface speed thereof independently. The periods of acceleration and deceleration of each of first, second, and third separation and transfer segments 54a, 54b, and 54c are provided by the offset crank motion which results from the second axis 70 of the drive ring 56 being offset from the first axis 60 of first, second, and third separation and transfer segments 54a, 54b, and 54c. Whereas, the periods of low speed dwell and high speed dwell are provided by the pivoting action of each coupler arm 78 about the pivot points 80 as the drive ring 56 is rotated. As such, the combination of the offset drive ring 56 and the pivoting coupler arm 78 of the apparatus 10 of the present invention can provide both the desired changes in speed and the desired periods of constant speed to effectively receive and apply the discrete elements 52 onto the second substrate web 20 in the desired spaced apart locations.

As compared to the conventional slip gap method for changing the speed of a discrete element such that it can be applied to a continuously moving web, the use of the combination of the offset drive ring 56 and the pivoting coupler arm 78 provides the ability to obtain greater changes in speed and to maintain constant speeds for a fixed duration. The fixed speed dwell achieved by using the oscillating cam adjusted roller or OSCAR module can be accurately and inexpensively designed to precisely control the length and placement of the discrete elements 52 on the second substrate web 20. For example, the drive ring 56 and coupler arm 78 may be analytically designed such that each of first, second, and third separation and transfer segments 54a, 54b, and 54c receives the discrete elements 52, while maintaining a constant surface speed substantially equal to the speed of the first substrate web 18 and applies the discrete elements 52 to the second substrate web 20, while maintaining a constant surface speed which is substantially equal to the speed of the second substrate web 20.

The surface speed of each of first, second, and third separation and transfer segments 54a, 54b, and 54c is maintained substantially constant as the discrete elements 52 are received or applied for at least about 10° of rotation and desirably at least about 20° of rotation of the respective transfer segment 54. For example, the surface speed of each of first, second, and third separation and transfer segments 54a, 54b, and 54c may be maintained substantially constant as the parts are received or applied for from about 5° to about 120° of rotation, desirably from about 15° to about 90° of rotation, and more desirably from about 45° to about 60° of rotation thereof. In addition, the surface speed increase or decrease of one of first, second, and third separation and transfer segments 54a, 54b, and 54c as it moves from receiving the discrete elements 52 to applying the discrete elements 52 and back again defines a speed ratio of from about 0.1:1 to about 0.99:1, desirably from about 0.38:1 to about 0.75:1, and more desirably, from about 0.4:1 to about 0.6:1. The term "speed ratio", as used herein, defines the ratio of the surface speed of each of first, second, and third separation and transfer segments 54a, 54b, and 54c at the low speed dwell to the surface speed of each of first, second, and third separation and transfer segments 54a, 54b, and 54c at the high speed dwell.

The above-described first and second embodiments of the apparatus 10 of the present invention may be used in the manufacture of absorbent articles 14, such as infant disposable diapers, child training pants, adult incontinence garments, feminine sanitary napkins, and other products for storing fluid bodily exudates. In operation, the apparatus 10 of the present invention performs a method of separating a discrete element 52 from a pre-perforated first substrate web 18' moving at a first speed and applying the discrete element 52 onto a second substrate web 20 moving at a second speed. The method includes the step of making lines of perforations 42 across a width W, at least partially through a thickness T, and at predetermined spaced apart intervals along a length L of the first substrate web 18. Then, the discrete element 52 is separated from the pre-perforated first substrate web 18' along a first of the lines of perforations 42. Once separated from the pre-perforated first substrate web 18', the discrete element 52 is placed or positioned on the second substrate web 20.

The step of making the lines of perforations 42 in the first substrate web 18 concludes with a pre-perforated first substrate web 18' being conveyed to a separation and transfer mechanism 12 having at least first, second, and third separation and transfer segments 54a, 54b, and 54c. The pre-perforated first substrate web 18' is moved onto an outer surface 64 of first and second separation and transfer segments 54a, 54b and held on the outer surface 64 of first and second separation and transfer segments 54a, 54b by means of vacuum.

The step of separating the discrete element 52 from the pre-perforated first substrate web 18' is done by accelerating the first separation and transfer segment 54a away from the second separation and transfer segment 54b, which is initially adjacent to the first separation and transfer segment 54a, to separate the discrete element 52 from the pre-perforated first substrate web 18' at the first of the lines of perforations 42.

The step of placing or positioning the discrete element 52 onto the second substrate web 20 may include one or two sub-steps. First, the separation and transfer mechanism 12 must be rotated around a central axis thereof in a range of from approximately 90° to approximately 180°. Then, after the separation and transfer mechanism is rotated, the first separation and transfer platform 54a, which is vacuum holding the discrete element 52 thereon, may be pivoted around an axis perpendicular to the central axis of the separation and transfer mechanism 12 in order to position the discrete element 52 in its correct orientation onto the second substrate web 20. If it is necessary to pivot the discrete element 52, the pivoting is usually somewhere in the range of from approximately 90° to approximately 180°.

In order to have the discrete element 52 be positioned on the second substrate web 20, a step of turning off vacuum may be needed so that the discrete element 52 is released from the outer surface 64 of the separation and transfer segment 54.

With respect to the second embodiment of the apparatus 10 of the present invention, a further step of applying adhesive to a first, outer surface (i.e., the surface of the pre-perforated first substrate web 18' which does not come into contact with the outer surface 64 of the separation and transfer segments 54) of the pre-perforated first substrate web 18' may be necessary in order to adhere the discrete element 52 to the second substrate web 20 once correctly positioned thereon. Most preferably, the step of applying adhesive would take place between the step of making the lines of perforations 42 in the first substrate web 18 and the step of separating the discrete element 52 from the pre-perforated first substrate web 18' by means of accelerating the first separation and transfer segment 54a to move away from the second separation and transfer segment 54b.

Also with respect to the second embodiment of the apparatus 10 of the present invention, another step of stretching or elongating a stretchable or elastic material of the first substrate web 18 may be necessary prior to the step of making lines of perforations 42 in the first substrate web 18, so that the discrete element 52 of stretchable material remains stretched both after being separated from the pre-perforated first substrate web 18' and after being transferred to the second substrate web 20.

Figure 5:
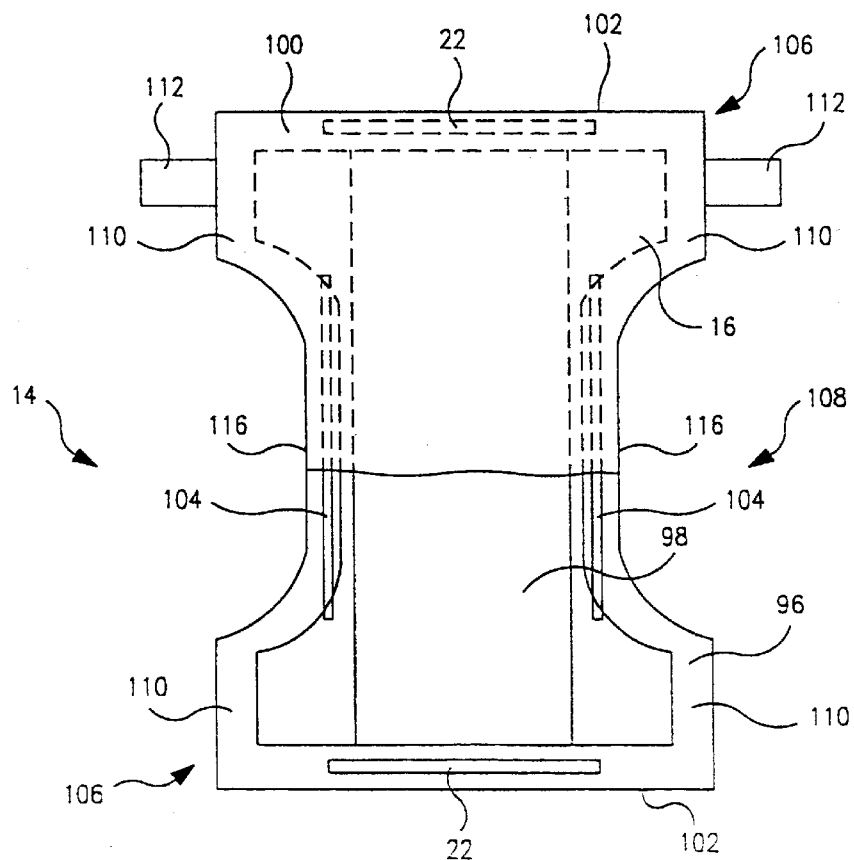
FIG. 5 is a representative view of a typical absorbent article, such as an infant disposable diaper or and an adult incontinence garment.

FIG. 5 generally illustrates that an absorbent article 14, such as an infant disposable diaper, a child training pant, an adult incontinence garment, a feminine sanitary napkin, and other similar products for storing fluid bodily exudates, which all have similar component parts, may be made by the method of the present invention with either of the first or second embodiment of the apparatus 10 of the present invention. More particularly, an absorbent article 14 often includes an absorbent core or insert member 16 and a liquid impermeable topsheet layer 96. The absorbent core member 16 is composed of a substantially hydrophilic material capable of absorbing a selected liquid, such as urine or other bodily discharges. The topsheet layer 96 is superposed in facing relationship with a first major surface of the absorbent core 16, and has an effective average pore size therein, which typically is larger than the pore size of the absorbent core 16. A liquid permeable transport layer 98 is located between absorbent core 16 and topsheet layer 96. The transport layer 98 is composed of a material which is less hydrophilic than the material of the absorbent core 16, and may generally be characterized as being substantially hydrophobic. The transport layer 98 has an effective average pore size therein which is greater than the pore size of the immediately adjacent portion of the absorbent core 16, but less than the pore size at topsheet 96. The transport layer 98 may have a density within the range of 0.015–0.5 g/cc, and a wet compression recovery value of at least about 65%.

An absorbent article 14 often includes a backsheet layer 100 and a substantially liquid permeable topsheet layer 96 superposed in facing relationship with the backsheet layer 100. An absorbent core 16, composed of a substantially hydrophilic material capable of absorbing a selected liquid, is located between backsheet layer 100 and topsheet layer 96, and a liquid permeable transport layer 98, composed of a substantially hydrophobic material, is located between topsheet 96 and absorbent core 16. The transport layer 98 has a substantially uniform density, and a wet compression recovery value of at least about 65% in the presence of water. Backsheet 100 and topsheet 96 are often essentially coterminous and extend out past the edges of absorbent core 16 to form first or end margins 102 and second or side margins 104. Absorbent article 14 may have waistband portions 106 interconnected by an intermediate portion 108.

The intermediate portion 108 may be narrower than the waistband portions 106, so that absorbent article 14 has a generally hourglass or I-shape platform with the waistband portions 106 defining ear sections 110 extending oppositely along the lateral cross-wise direction. Two ear sections 110 at one of waistband portions 106 include securement means for fastening the absorbent article 14 to the wearer thereof. The securement means may be operably connected to the back waistband portion 106 of the absorbent article 14 and comprise adhesive tape tabs 112. It is readily apparent, however, that various other securement means, such as hooks, snaps, cohesive strips, and similar, could also be employed as fastening means. Further, leg elastic members 114 may be attached to each of the side margins 104 of the absorbent article 14. The leg elastic members 114 may be configured so as to gather and shirr the leg band portions of the absorbent article 14 to form seals or gaskets about the legs of the wearer. Absorbent article 14 may include waist elastic members 22 secured to one or more of end margins 102 to gather and shirr the waistband portions 106 of the absorbent article 14. The absorbent article 14 may include a generally rectangular-shaped absorbent core 16 and perforations formed through the side margins 104 of backsheet layer 100. The perforations may have diameters up to about 0.020" and may be arranged to provide about 100–300 perforations per square inch of backsheet area. Preferably, the perforated area is limited to the portion of the side margins 104 of the backsheet 100 located between the leg elastic member and the terminal side edge of the backsheet 100, but may cover a greater portion or even all of the area of the backsheet 100, if desired.

The various components of absorbent article 14 are assembled together employing conventional techniques. For example, the components may be attached to one another employing thermal or sonic bonds, or mechanical fasteners, such as snaps or clips. Alternatively, the components can be attached with adhesives, such as hot melt pressure-sensitive adhesives. The adhesives can be applied by employing conventional techniques, such as spraying droplets or filaments of adhesive. Preferably, the components are assembled employing a plurality of generally parallel lines of hot melt pressure-sensitive adhesive oriented along the length dimension of the absorbent article 14.

Backsheet 100 may be composed of liquid impermeable material, such as polymer film. For example, backsheet 100 can be composed of a polyolefin film, such as polyethylene or polypropylene. Backsheet 100 can also be composed of a liquid impermeable, but vapor permeable material, such as breathable, micro-porous polyethylene film, or the backsheet 100 can be composed of a vapor permeable, nonwoven fibrous material which has been suitably treated to impart a desired degree of liquid impermeability. For example, the backsheet 100 may be comprised of a nonwoven spunbounded layer which has been completely or partially coated with a polymer film to provide liquid impermeability in particular areas.

Topsheet 96 is typically composed of a liquid permeable, substantially hydrophobic fibrous material, such as a spunbonded web composed of synthetic polymer filaments. Alternatively, topsheet 96 may comprise a meltblown web or a bonded-carded-web composed of synthetic polymer filaments. Suitable synthetic polymers include, for example, polyethylene, polypropylene, and polyesters. The polymer filaments generally have a denier within the range of about 1.5–7, and preferably have a denier within the range of about 1.5–3. The filaments are arranged to form a layer having a basis weight with the range of about 0.6–1.0 oz/yd$^2$ (osy), and preferably a basis weight of about 0.8 osy. In addition, the topsheet layer 96 has a bulk thickness with the range of about 0.008–0.017", and preferably a bulk thickness within the range of about 0.010–0.012" for improved effectiveness. The bulk thickness is measured under a restraining pressure of 0.014". The topsheet 96 has a pore size that readily allows the passage therethrough of liquids, such as urine and other bodily exudates. A typical topsheet 96 may have an effective average pore size, in terms of equivalent circular diameter (ECD), which is within the range of about 40–110 μm, and preferably within the range of about 70–110 μm to provide improved effectiveness.

The topsheet 96 can optionally be treated with surfactants to adjust the degree of hydrophobicity and wettability, and can also be selectively embossed or apertured with discrete slits or holes extending therethrough. When configures with apertures, the apertures may substantially define the effective pore size of the topsheet 96. The apertures have an average equivalent diameter within the range of about 138–350 μm and preferably have an average diameter of about 250 μm to provide improved performance. Thus, the topsheet 96 would again have a pore size which is larger than the pore size of transport layer 98.

Absorbent core 16 typically comprises a pad composed of airlaid cellulosic fibers commonly referred to as wood pulp fluff. Conventional pads can have a density ranging from about 0.05–0.20 g/cc, and are sufficiently flexible to readily conform to the body of the wearer. Absorbent core 16 may also comprise a co-form material composed of a mixture of cellulosic fibers and synthetic polymer fibers. For example, the co-form material may comprise an airlaid blend of cellulosic fibers and meltblown polyolefin fibers, such as polyethylene and polypropylene fibers. The fibrous material comprising absorbent core 16 may be composed of filaments having a coarseness of about 10–20 mg per 100 m, and preferably having a coarseness within the range of about 10–18 mg per 100 m. The filaments are arranged to form a layer having a basis weight within the range of about 400–1200 g/m$^2$ and preferably a basis weight of about 800 g/m$^2$. In addition, the material of absorbent core 16 has a bulk thickness within the range of about 0.17–0.21", as measured under a restraining pressure of 0.068 psi.

Absorbent core 16 may also include an effective amount of an inorganic or organic high-absorbency material to enhance the absorptive capacity of the absorbent core 16. For example, absorbent core 16 can include 5–95 wt % high-absorbency material, and preferably includes about 10–30 wt % of the high-absorbency material to provide more efficient performance. Suitable inorganic high-absorbency materials can include, for example, absorbent clays and silica gels. Organic high-absorbency materials can include natural materials, such as agar, pectin, guar gum, and peat moss, as well as synthetic materials, such as synthetic hydrogel polymers. Such hydrogel polymers include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine and similar. Other suitable polymers include hydrolyzed acrylonitrile grafted starch, acrylic grafted starch, and isobutylene maleic anhydride copolymers, and mixtures thereof. The hydrogel polymers are preferably lightly cross-linked to render the material substantially water-insoluble. Cross-linking may, for example, be by irradiation or by covalent, ionic, Van der Waals, or hydrogen bonding. Suitable materials are available from various commercial vendors, such as Dow Chemical Company, Celanese Corporation, Allied-Colloid, and Stockhausen. Typically, the high-absorbency material is capable of absorbing at least about 15 times its weight in water, and preferably is capable of absorbing at least about 25–50 times its weight in water.

The high-absorbency material can be distributed or otherwise incorporated into absorbent core 16 employing various techniques. For example, the high-absorbency material can be substantially uniformly distributed in the mass of fibers comprising the absorbent core 16. The material can also be non-uniformly distributed among the fibers to form, for example, a generally continuous gradient with either an increasing or decreasing concentration of high-absorbency material, as determined by observing the concentration moving from the body-side of absorbent core 16 to the outer-side of the absorbent core 16. Alternatively, the high-absorbency material can comprise one or more discrete layers or strips selectively segregated from the fibrous material of absorbent core 16.

The apparatus 10 can be used to apply elongated elastic parts to the waist opening regions on a product web of interconnected disposable diapers as will be described with respect to the second embodiment of the present invention. For example, a continuously moving first substrate web 18 of elongated elastic material is perforated and then separated at the junction of adjacent ones of first, second, and third separation and transfer segments 54a, 54b, and 54c. The web of elastic material may be elongated at least about 150% and desirably from about 150% to about 400% before being perforated and separated. The discrete elongated elastic elements 52 are held onto the outer surface 64 of each of first, second, and third separation and transfer segments 54a, 54b, and 54c as it rotates in the elongated state by the surface roughness of the outer surface 64. In a particular aspect, the discrete elongated elastic elements 52 are maintained at an elongation of at least about 125%, desirably at least about 150%, and more desirably from about 150% to about 400% until they are applied to the product web 20. In addition, a relatively low level of vacuum may also be drawn through holes in the outer surface 64 to assist the surface roughness in maintaining the discrete elongated elastic elements 52 in the elongated state.

The combination of the offset drive ring 56 and the pivoting coupler arm 78 are rotated by the drive means which, in turn, rotates each of first, second, and third separation and transfer segments 54a, 54b, and 54c at the desired variable speed with fixed speed dwells. As each of first, second, and third separation and transfer segments 54a, 54b, and 54c is rotated, the outer surface 64 thereof maintains a substantially constant speed as the discrete elongated elastic elements 52 are received and applied. In particular, each of first, second, and third separation and transfer segments 54a, 54b, and 54c receives the discrete elongated elastic elements 52, while maintaining a constant surface speed substantially equal to the speed of the first substrate web 18 of discrete elongated elastic elements 52 prior to separation. The surface speed of each of first, second, and third separation and transfer segments 54a, 54b, and 54c then changes to a second constant surface speed such that the speed of the discrete elongated elastic elements 52 being transferred is substantially equal to the speed of the continuously moving product web of interconnected diapers as the discrete elongated elastic elements 52 are applied to the waist opening regions on each diaper. The surface speed of each of first, second, and third separation and transfer segments 54a, 54b, and 54c is then changed back to substantially equal the speed of the first substrate web 18 of discrete elongated elastic material elements 52 before the next discrete elongated elastic element 52 is received.

The discrete elongated elastic elements 52 being applied to the second substrate web 20 of interconnected diapers may be made of any suitable material having elastic or stretchable properties. Examples of such materials include films or layers of natural rubber, synthetic rubber, or thermoplastic elastomeric polymers, and can be panels, or single, or multiple threads or filaments or ribbons thereof. These materials may also be heat-shrinkable or heat-elasticizable.

Furthermore, these stretchable materials may be formed with gatherable layers, such as spunbonded polymer materials, as a stretch-bonded laminate. For example, a suitable stretch-bonded laminate comprises two gatherable layers of 0.04 osy of spunbond polypropylene having therebetween a layer of meltblown elastic material such as a Kraton elastic in either layer form or separate threads of material having a basis weight of about 0.50 osy. The layer of the elastomeric is stretched, the two layers of polypropylene then joined to the elastomeric layer, and upon relaxing the layers, the polypropylene layers gather. The materials may be breathable or non-breathable.

Although the above representative example concerns the application of leg elastic to a diaper, it should be readily apparent to those of ordinary skill in the art that the present invention may be utilized in any circumstance requiring speed variations and constant speed dwells when transferring parts onto a moving web.

While the invention has been described in detail with respect to specific aspects thereof, it will be appreciated that those skilled in the art upon attaining an understanding of the foregoing, may readily conceive of alterations to, variations of, and equivalents to these aspects. Accordingly, the scope of the present invention should be assessed as that of the appended claims and any equivalents thereto.

We claim:

1. Apparatus for separating discrete elements, in sequence, from a first substrate web moving at a first speed and applying the discrete elements onto a second substrate moving at a second speed, said apparatus comprising:

(a) a first station for making lines of perforations across a width, at least partially through a thickness, and at predetermined spaced apart intervals along a length of the first substrate web;

(b) a second station, comprising a separation and transfer mechanism, for sequentially separating the discrete elements from the first substrate web at respective lines of perforations, by tearing respective lines of perforations, and placing the discrete elements onto the second substrate, said separation and transfer mechanism comprising a plurality of separation and transfer segments which tear the web at the respective lines of perforation, thereby to develop the respective discrete elements, by accelerating a speed of advance of the web adjacent the respective line of perforations, said plurality of separation and transfer segments being mounted about a common axis, and advancing respective ones of the discrete elements about the common axis in placing the discrete elements onto the second substrate; and (c) a third station, comprising an adhesive applicator, for applying adhesive to a first outer surface of the first substrate web which first outer surface is the surface of the substrate web which does not come into contact with the outer surface of said separation and transfer mechanism.

2. Apparatus as in claim 1 wherein said first station includes a perforation cutter assembly having first and second rollers, said first roller having at least one anvil member having a flat cutting surface for being cut against, said at least one anvil member being partially embedded in and having said flat cutting surface extending radially outwardly from an outer circumferential surface of said first roller, and said second roller having at least one discontinuous cutting blade extending from an outer circumferential surface thereof, whereby said first and second rollers are timed to rotate so that said at least one cutting blade interacts with the flat cutting surface of said at least one anvil member to make the lines of perforations at such spaced intervals along the length of the first substrate web to form the pre-perforated first substrate web.

3. Apparatus as in claim 2 wherein said at least one discontinuous cutting blade comprises a rectangular metal plate having two long sides, each long side having a discontinuous cutting edge.

4. Apparatus as in claim 3 wherein said first station further includes an elongate conveyor assembly for conveying the pre-perforated first substrate web from said perforation assembly to said second station.

5. Apparatus as in claim 2, further comprising a web guide located prior to said second station, wherein said web guide keeps the first substrate web centered during operation of said apparatus.

6. Apparatus as in claim 1 wherein said plurality of separation and transfer segments includes first, second, and third separation and transfer segments.

7. Apparatus as in claim 6 wherein said first, second, and third separation and transfer segments each include holding structure for holding the pre-perforated first substrate web against an outer surface thereof and for holding the discrete element, once separated from the pre-perforated first substrate web, against an outer surface thereof.

8. Apparatus as in claim 7 wherein said holding structure comprises the outer surface being textured to define a surface roughness of about 5 $\mu$m up to about 50 $\mu$m.

9. Apparatus as in claim 1 wherein said adhesive applicator is located between said first and second stations and applies the adhesive (i) after formation of a respective one of the lines of perforations, to a portion of the web which is between the respective line of perforations and a leading edge of the web, and (ii) before the respective portion of the web arrives at the second station.

10. Apparatus as in claim 1, said apparatus being designed and configured to so grip the discrete element and the first substrate web that, when the first substrate web comprises stretchable material which has been stretched prior to entering said first station, the discrete element and the first substrate web remain stretched after the discrete element is separated from the first substrate web and when the discrete element is transferred from said second station onto the second substrate web.

* * * * *